United States Patent
Hu et al.

(10) Patent No.: US 7,497,900 B2
(45) Date of Patent: Mar. 3, 2009

(54) TWO-PART BORATE, SILICATE AND ZINC COMPOSITIONS, AND METHODS FOR TREATING WOOD PRODUCTS

(75) Inventors: Yatao Hu, Malvern, PA (US); Jason D. Lenox, Boyertown, PA (US); Neil T. Miller, King of Prussia, PA (US); David M. Schubert, Lone Tree, CO (US)

(73) Assignees: PQ Corporation, Berwyn, PA (US); U.S. Borax Inc., Greenwood Village, CO (US)

( * ) Notice: Subject to any disclaimer, the term of this patent is extended or adjusted under 35 U.S.C. 154(b) by 0 days.

(21) Appl. No.: 11/547,377

(22) PCT Filed: Mar. 31, 2005

(86) PCT No.: PCT/US2005/010793

§ 371 (c)(1),
(2), (4) Date: Oct. 29, 2007

(87) PCT Pub. No.: WO2005/096822

PCT Pub. Date: Oct. 20, 2005

(65) Prior Publication Data

US 2008/0124478 A1   May 29, 2008

Related U.S. Application Data

(60) Provisional application No. 60/559,485, filed on Apr. 3, 2004.

(51) Int. Cl.
*A01N 59/14* (2006.01)
*A01N 59/16* (2006.01)

(52) U.S. Cl. .............. 106/18.32; 106/15.05; 106/18.12; 106/18.36; 252/385; 424/641; 424/DIG. 11

(58) Field of Classification Search .............. 106/15.05, 106/18.12, 18.3, 18.36; 424/641, DIG. 11; 427/297, 394, 395, 397, 397.8, 440; 428/527.1; 252/385

See application file for complete search history.

(56) References Cited

U.S. PATENT DOCUMENTS

| | | | |
|---|---|---|---|
| 2,194,827 A | 3/1940 | Gordon | |
| 3,306,765 A | 2/1967 | Du Fresne et al. | |
| 3,974,318 A | 8/1976 | Lilla | |
| 4,656,060 A * | 4/1987 | Krzyzewski | 427/397 |
| 4,731,265 A | 3/1988 | Hirao et al. | |
| 4,857,365 A | 8/1989 | Hirao et al. | |
| 5,207,823 A * | 5/1993 | Shiozawa | 106/18.13 |
| 5,478,598 A * | 12/1995 | Shiozawa | 427/297 |
| 6,146,766 A | 11/2000 | Slimak et al. | |
| 6,303,234 B1 | 10/2001 | Slimak et al. | |
| 6,896,908 B2 * | 5/2005 | Lloyd et al. | 424/635 |
| 2001/0002282 A1 | 5/2001 | Grantham et al. | |
| 2003/0104135 A1 | 6/2003 | Grantham et al. | |
| 2004/0166246 A1 | 8/2004 | Holcomb | |
| 2008/0069978 A1 | 3/2008 | Lenox et al. | |
| 2008/0166481 A1 | 7/2008 | Hu et al. | |

FOREIGN PATENT DOCUMENTS

| | | |
|---|---|---|
| JP | 56-25363 A | 6/1980 |
| JP | 06336408 A2 | 12/1994 |
| JP | 1995251403 A | 10/1995 |
| JP | 2000-108108 A * | 4/2000 |
| WO | WO 01/70472 A1 | 9/2001 |
| WO | WO 2005/094586 | 10/2005 |
| WO | WO 2005/096821 | 10/2005 |

OTHER PUBLICATIONS

Furno, T. et al., "Combinations of wood and silicate Part 6. biological resistances of wood-mineral composites using water glass-boron compound system", Wood Science and Technology, 32 (1998) pp. 161-170, Springer-Verlag 1998. [no month].

Dev, Indra et al., "Terminte resistance and permanency tests on zinc-borate—an environmental friendly preservative", J. Timb. Dev. Assoc. (India), vol. XLIII, No. 2, Apr. 1997.

* cited by examiner

*Primary Examiner*—Anthony J Green
(74) *Attorney, Agent, or Firm*—Kurt R. Ganderup

(57) ABSTRACT

Systems and methods are provided for treating products containing wood fibers to provide protection against wood destroying organisms and fire, and resistance against leaching of the preservative from the wood by water in exposed environments such as exterior applications. The methods involve applying to a substrate a first aqueous composition containing a boron compound, a source of zinc, and ammonia, followed by application of a second aqueous composition containing an alkali metal silicate. The compositions may be applied by vacuum and/or pressure treatment or dip treatment under atmospheric pressure.

13 Claims, No Drawings

TWO-PART BORATE, SILICATE AND ZINC COMPOSITIONS, AND METHODS FOR TREATING WOOD PRODUCTS

This application is the national stage of International Application No. PCT/US2005/010793 filed on Mar. 31, 2005, which claims the benefit of U.S. Provisional Application No. 60/559,485, filed on Apr. 3, 2004, the entire contents of which are incorporated herein by reference.

FIELD OF THE INVENTION

This invention relates to the preservation of wood and more particularly, the invention provides compositions and methods for treating wood and wood products to provide leach-resistant protection against insect and fungal attack, as well as resistance to fire.

BACKGROUND OF THE INVENTION

Inorganic borate compounds have been used as wood preservatives for many years for protection against termites and other wood destroying insects, as well as fungal decay. Soluble borates such as borax, boric acid and disodium octaborate tetrahydrate are well known preservatives in aqueous-based systems for treating solid wood for use in protected environments. However, due to their water solubility they are readily leached from treated wood in exposed environments such as exterior and ground contact applications.

Copper chrome arsenate (CCA) is a leach-resistant wood preservative that has been used for many years to treat solid wood for use in exterior applications. However, due to environmental health and safety issues, and toxicity concerns relating to the constituent metals, particularly arsenic, CCA has come under increasing regulatory pressure and is being phased out of use in many areas. Even compositions containing copper without chromium or arsenic are coming into disfavor for environmental reasons, and thus it is desirable to reduce or eliminate copper content as well.

Solid zinc borate has proven very useful as a preservative for wood composites, where it is added as a solid material during manufacture of the composites. The inherent low solubility of zinc borate makes it resistant to leaching, even in high moisture environments. However, in view of its low solubility, it is not so easy to treat solid lumber with zinc borate. Dev et al. (J. Timb. Dev. Assoc., 1997) describes a two-stage process for treating solid wood with zinc borate which involved impregnating the wood with solutions of borax and zinc in two separate steps.

Ammonia-based solutions have been proposed to solubilize metals such as zinc and copper in an attempt to fix borates in wood. U.S. Pat. No. 2,194,827 (Gordon) discloses an aqueous ammonia solution of copper, zinc and borate salts for the treatment of wood.

U.S. Pat. No. 3,974,318 to Lilla discloses a method for fire retarding and preserving wood products, paper, cardboard, boxboard, cloth and other porous materials having a plurality of internal voids, in which a water soluble silicate composition is applied to the porous materials, penetrating into the voids, followed by drying the material. Thereafter, a water soluble metallic salt composition is applied, also penetrating into the voids and reacting in situ to form a water insoluble metallic silicate with a high degree of water of hydration disposed throughout the voids.

Shiozawa (U.S. Pat. No. 5,478,598) discloses a wood preservative composition that includes a first solution having: a copper compound selected from the group consisting of copper borate, copper hydroxide, copper acetate, copper chloride, and copper sulfate; a zinc compound selected from the group consisting of zinc borate, zinc acetate, zinc hydroxide, zinc oxide, zinc chloride, and zinc sulfate; and/or a boron compound selected from the group consisting of boric acid and borax; sodium silicate, and a second solution having rare earth chloride or alkaline earth chloride. The inventor states that the inventive composition can be retained in the wood while the leaching thereof out of the wood is prevented.

SUMMARY OF THE INVENTION

In one aspect, the invention provides a preservative system comprising:
(a) a first aqueous composition comprising a source of zinc selected from the group consisting of zinc oxide and soluble zinc salts; a source of borate selected from the group consisting of zinc borate, boric acid, boric oxide and water soluble borate salts; a source of ammonia; and water; wherein the composition comprises at least 50 wt % water; and
(b) a second aqueous composition, separate from the first composition, comprising an alkali metal silicate and water.

In another aspect, the invention provides a preservative system consisting of:
(a) a first aqueous composition consisting essentially of a source of zinc selected from the group consisting of zinc oxide and soluble zinc salts; a source of borate selected from the group consisting of zinc borate, boric acid, boric oxide and water soluble borate salts; a source of ammonia; and water; wherein the composition is essentially copper-free and comprises at least 50 wt % water; and
(b) a second aqueous composition, separate from the first composition, consisting essentially of an alkali metal silicate and water.

In still another aspect, the invention provides a method for preserving an article comprising wood fibers, the method comprising the steps of:
(a) applying to the article a first aqueous composition prepared by combining ingredients comprising:
   i) a source of zinc selected from the group consisting of zinc oxide and soluble zinc salts;
   ii) a source of borate selected from the group consisting of zinc borate, boric acid, boric oxide and water soluble borate salts;
   iii) a source of ammonia; and
   iv) water;

such that the first aqueous composition penetrates into the wood fibers, wherein the composition comprises at least 50 wt % of water;
(b) applying to the article a second aqueous composition comprising an alkali metal silicate and water; and
(c) drying the wood fibers;

such that there is deposited therein a bioeffective amount of a residual component comprising zinc, boron, and silicon.

In yet another aspect, the invention provides an article comprising wood fibers comprising a residual component comprising zinc, boron, and silicon, prepared by treating the wood fibers according to the method set forth in the immediately preceding paragraph.

In still another aspect, the invention provides a method of treating a substrate comprising wood fibers to provide resistance to flame spread, the method comprising the steps of:
(a) applying to the article a first aqueous composition prepared by combining ingredients comprising:

i) a source of zinc selected from the group consisting of zinc oxide and soluble zinc salts;

ii) a source of borate selected from the group consisting of zinc borate, boric acid, boric oxide and water soluble borate salts;

iii) a source of ammonia; and iv) water;

such that the first aqueous composition penetrates into the wood fibers, wherein the composition comprises at least 50 wt % of water;

(b) applying to the article a second aqueous composition comprising an alkali metal silicate and water; and (c) drying the wood fibers;

such that there is deposited therein a flame retardant amount of a residual component comprising zinc, boron, and silicon.

DETAILED DESCRIPTION OF THE INVENTION

The invention provides a system and method for preservative treatment of items comprising wood fibers. The method involves first treating the item with a first aqueous composition comprising ammonia-stabilized zinc and borate, followed by treatment of the item with a second aqueous composition containing silicate. The preservative compositions are useful in the treatment of such items to provide borate leach-resistant protection against wood destroying organisms such as termites or other wood destroying insects, and decay fungi. They may also provide other benefits to items with which they are treated, including providing resistance to fire. The compositions may contain copper, or may be essentially copper free, by which it is meant that copper, if present at all, is present only as an impurity in the compositions of this invention, and is not purposely added. In any case, compositions that are "essentially copper free" contain less than 0.1% copper by weight.

As used herein, the term "residual component" refers to a material comprising zinc, boron, and silicon that remains in an article after being contacted with a composition according to the invention. It will be understood that the residual component may vary in composition according to the exact ratio and identity of the zinc, boron, and silicate sources used in the treatment compositions, as well as the amount and type of other materials that may be included in the compositions.

As used herein, the term "bioeffective amount" as applied to a residual component means an amount of material sufficient to reduce or eliminate attack or residence on a treated article by one or both of an insect and a fungus that causes rot. Such reduction or elimination may be by any means, including but not limited to repelling, killing, and prevention of growth on or in the treated article.

As used herein, the term "flame retardant amount" as applied to a residual component means an amount of material sufficient to reduce or eliminate flame spread on a treated article.

As used herein, the term "essentially chloride ion free" means that none of the ingredients comprises chloride ion, other than as an impurity. In any case, a composition that is "essentially chloride free" contains less than 0.1% chlorine by weight.

As used herein, the term "sodium borate" means one or more of disodium octaborate tetrahydrate, sodium tetraborate decahydrate (borax), sodium tetraborate pentahydrate, sodium tetraborate (anhydrous borax), sodium metaborate, sodium pentaborate, and mixtures of any of these. The term "water soluble borate salt" means any sodium borate, any analogous potassium borate, any analogous ammonium borate, or mixtures of any of these.

References to amounts of ammonia or amines in a composition refer to the amount of that material calculated as its unbound form, although it will be understood that equilibrium processes may cause at least some of the compound to be in the form of a salt or other chemical species.

The preferred concentrations for the first aqueous composition are between about 0.1 and 1 percent by weight boron (B), between about 0.2 and 2.5 percent by weight zinc (Zn) and between about 1 and 5 percent by weight ammonia ($NH_3$). The preferred zinc to boron (Zn:B) mole ratio in the first aqueous composition is at least 0.4:1, typically at least 1:1, and more typically at least 1.5:1. The preferred ratio is at most 5:1, typically at most 3:1, and more typically at most 2:1. The preferred ammonia to zinc ($NH_3$:Zn) mole ratio in the first aqueous composition is in the range of about 7:1 to about 33:1. The first and second compositions are aqueous mixtures, and are kept in separate containers and applied sequentially to the substrate being treated. It has been found that choice of Zn:B and $NH_3$:Zn ratios within the ranges specified above, combined with the absolute concentration ranges set forth above, provides compositions having both good shelf life stability against gelling and precipitation and high resistance to leach-out of borate in items treated with the compositions. The first and second compositions typically each contain at least 50 wt % water, but compositions having a higher concentration of active ingredients and a less than 50% water content may be used according to the invention. Such compositions may, for example, be kept as concentrates and diluted as needed prior to application.

The second aqueous composition is prepared by dissolving a soluble silicate compound in water. Suitable nonlimiting examples of soluble silicate compounds include alkali metal silicates and ammonium silicates. A liquid or water-soluble solid form of silicate may be used. Preferred silicates include the alkali metal silicates, e.g. sodium or potassium silicate, in liquid form. Preferably the alkali metal silicate is sodium silicate, and more preferably it is sodium silicate having an $SiO_2$:$Na_2O$ weight ratio greater than 3:1. Most preferably the sodium silicate has a silicate to sodium ($SiO_2$:$Na_2O$) weight ratio of about 3.22:1. Such materials are commercially available under the trade names N®Silicate and N®Clear, sold by the PQ Corporation of Valley Forge, Pa. The concentration of the $SiO_2$ in the second aqueous composition may be between about 1 and 10 wt % $SiO_2$, according to the invention. Typically, the concentration will be about 4 wt % $SiO_2$.

Higher molar Zn/B ratios reduce leaching of borate from substrate, provided that the resulting compositions do not suffer significant precipitation or gelation. Upper limits of Zn/B may however be imposed by practical considerations regarding stability of the formulation, and/or by precipitation or gelling reactions that occur due to the interaction of high concentrations of zinc with other ingredients.

Zinc Sources

Suitable sources of zinc for use according to the invention may be provided in the form of various zinc compounds including zinc oxide, zinc chloride, zinc acetate, zinc sulfate, and other water-soluble zinc salts. Other zinc salts such as zinc naphthenate, zinc acetylacetonate, zinc gluconate, and zinc complexes with chelating agents such as EDTA may also be used according to the invention. Alternatively, zinc borate may be used. In some embodiments of the invention, zinc chloride is a preferred source of zinc. In other embodiments, for example where it is desired to reduce the chloride ion content in the composition for purposes such as prevention of corrosion, zinc acetate or zinc sulfate may be preferred. Zinc serves to reduce the tendency of borate to leach from the wood upon exposure to water after it has been treated, possibly by formation of a zinc borate precipitate which is not readily soluble in water. Zinc may also contribute to the biocidal properties of the preservative compositions of the present invention. Ammonia, such as in the form of ammonium hydroxide ($NH_4OH$), aids the dissolution of zinc in the first aqueous composition.

Source of Borate

Suitable source of borate for use according to the invention include boric acid and the water-soluble salts thereof. Alternatively, zinc borate may be used. Preferred source of borates include the sodium borates, such as disodium octaborate tetrahydrate (commercially available as TIM-BOR® Industrial wood preservative manufactured by U.S. Borax Inc., Valencia, Calif.), sodium tetraborate decahydrate (borax), sodium tetraborate pentahydrate, anhydrous sodium tetraborate, sodium metaborate and sodium pentaborate, as well as other alkali metal borates and ammonium borates such as potassium tetraborate, potassium metaborate and ammonium pentaborate. Boric acid and boron oxide may also be used.

Preparation of First Aqueous Composition

The first aqueous composition of the present invention is preferably prepared by dissolving a zinc compound in an aqueous ammonia solution, followed by the addition of a source of borate and agitating until essentially all solids are dissolved. The source of borate is preferably pre-dissolved in water prior to adding to the ammonia stabilized zinc solution. Vigorous mixing is recommended to promote the rapid dissolution of zinc and borate solid compounds in solution.

It has been found that mere dissolution of zinc borate in ammonia provides preservative compositions with poor borate leach performance; that is, wood treated with such compositions loses borate content when contacted with water over an extended period of time, as measured by test method AWPA E11-97. In contrast, wood that has been treated with compositions prepared according to the invention show notably lower borate leach rates, and therefore may be expected to retain their preservative activity for a longer time.

Source of Ammonia

Suitable sources of ammonia for use according to the invention may include, as nonlimiting examples, aqueous ammonium hydroxide and anhydrous ammonia.

Wood Fibers

Wood fibers according to the invention may be fibers in a piece of wood, or fibers freed from wood by a pulping operation such as is commonly performed in the pulp and paper industry, i.e. wood pulp. As used herein, the term "wood" is to be understood according to its common use, and includes wood pieces or particles of any size or shape, including for example sawn lumber, plywood, oriented strand board, particle board, ground wood, sawdust, and wood/polymer composite materials. The term "wood" according to this use therefore refers to wood that has not been subjected to a pulping operation.

As used herein, the term "wood pulp" refers to wood that has been subjected to a pulping operation, including but not limited to Kraft pulping, sulfite pulping, and chemi-thermomechanical pulping. Wood pulp treated according to the invention may be in any form, including but not limited to unconsolidated (loose) pulp fibers, including for example blown insulation, and paper. Paper that comprises wood pulp treated according to the invention may be paper in any form, including but not limited to sheet paper, corrugated board, and paper comprising a surface of gypsum wallboard.

Application of the Preservative Compositions

The preservative compositions may be applied to the item to be treated by any commercially acceptable method, as long as sufficient composition penetrates into the item so as to result in the deposition of a bioeffective or fire retardant amount of a residual component. It should be noted that the residual component, which is the material that is active for deterrence of biological attack or attack by fire, may comprise zinc, boron, and/or silicon in the form of the compounds that were used to prepare the compositions. They may however represent the result of subsequent chemical reactions in the treated substrate. One possible nonlimiting example is formation of zinc borate in the treated article, but other chemical reactions may occur in addition or instead, or none may occur at all. Similarly, ammonia may be chemically bound in the treated item, or it may be essentially absent due to other chemical reactions or to volatilization out of the item. Regardless of the exact form and location of the zinc, boron, ammonia, and silicon after the treatment is complete, there remains a residual component that provides the preservative properties of the invention. Resistance to insects, wood-decay fungi, and/or fire is thereby achieved.

The composition containing zinc and borate is applied first to the item to be treated. After completing the treatment with the zinc/borate solution, the item is treated with the silicate composition. The relative amounts of first and second aqueous compositions applied to the item are such that there is sufficient Si content to immobilize substantially the components of the treatment system in the substrate. In one exemplary embodiment of the invention, the molar ratio of Si/Zn is about 0.6:1, although higher or lower ratios may be used. In general, higher levels of silicate appear to improve immobilization of the components.

For wood products, application of the first and/or second compositions may involve a method such as vacuum and/or pressure treatment or dip treatment under atmospheric pressure. Preferably, treatment may involve both vacuum and pressure, wherein a vacuum is first applied to the wood product, prior to application of the first and/or second aqueous composition. The solution is then applied to the wood product and pressure is then applied to force the solution into the pores of the wood. Preferably, after the wood product has been treated, the treated wood may be dried to improve the leach resistant properties of the wood. Drying may be performed at an elevated temperature, preferably no higher than 90° C., even more preferably no higher than 70° C., with about 60° C. being typical. It has been found that the use of lower drying temperatures for a given amount of drying time tends to reduce the borate leach rate of items treated with these compositions. Thus in some embodiments of the invention, drying is performed under ambient temperatures, typically between about 20° C. and 25° C., optionally aided by the use of vacuum or blown air. Methods for drying wood, and the desired moisture level of dried wood, are well known in the art.

For applications in which resistance to biological attack is the desired result, it is believed that the amount of borate in the treated substrate should be at least 0.1%, measured as boric acid equivalents (BAE). A level of at least 0.5% will typically be used. In general, increased BAE provides increased resistance to biological activity, as well as to fire. Methods for applying the compositions include spraying, roll coating, dipping, and any other means known in the art relevant to the particular form of the wood or wood pulp.

EXAMPLES

Example 1

A series of five ammonia-stabilized zinc and borate-containing solutions, each having a zinc to boron (Zn:B) mole ratio of 0.4:1, were prepared according to the methods of the invention, as examples of the first aqueous composition. The solution concentrations for the five solutions were designed to provide target retentions of about 0.13%, 0.25%, 0.50%, 0.75% and 1.5% $B_2O_3$ in the wood after treatment. The amounts of each ingredient used in each of the five solutions, and the resulting concentrations of boron, zinc, and ammonia, are summarized in Table I. The method of preparation is described below, using the target 0.75% $B_2O_3$ solution as an example.

Ammonium hydroxide (69 mL of a 30% $NH_{40}H$ solution) was stirred into 200.00 g of deionized water. Zinc chloride (10.36 g $ZnCl_2$) was added to the water-ammonia solution and the mixture was vigorously stirred until the zinc chloride was completely dissolved. In a separate container, 9.80 g of TIM-BOR® disodium octaborate tetrahydrate (manufactured by U.S. Borax Inc.) was dissolved in 110.89 g deionized water. The TIM-BOR® solution was then poured slowly with agitation into the zinc/ammonia solution, providing an essentially clear solution containing 0.51% B, 1.24% Zn, and 2.51% $NH_3$.

A series of five solutions of sodium silicate was prepared as follows, each paired with one of the ammonia stabilized zinc and borate compositions described above. In a separate container, the amount of N®Silicate (manufactured by PQ Corporation, Valley Forge, Pa.) indicated in Table I was added to the indicated amount of deionized water and stirred until the silicate was completely dispersed. The resulting solution was the second aqueous composition.

TABLE I

| Comp. No. | | Target % $B_2O_3$ in Wood | | | | |
|---|---|---|---|---|---|---|
| | | 0.13 | 0.25 | 0.50 | 0.75 | 1.50 |
| 1 | $H_2O$ (g) | 227.51 | 225.82 | 222.44 | 200.00 | 121.50 |
| 1 | 30% $NH_4OH$ (mL) | 50 | 50 | 50 | 69 | 137 |
| 1 | $ZnCl_2$ (g) | 1.80 | 3.49 | 6.87 | 10.36 | 20.62 |
| 1 | $H_2O$ (g) | 118.99 | 117.39 | 114.19 | 110.89 | 101.19 |
| 1 | TIM-BOR (g) | 1.70 | 3.30 | 6.50 | 9.80 | 19.50 |
| 2 | $H_2O$ (g) | 280.89 | 279.29 | 276.10 | 272.80 | 263.11 |
| 2 | N-Silicate (g) | 1.70 | 3.30 | 6.49 | 9.79 | 19.48 |
| 1 | Wt. % Boron (B) | 0.09 | 0.17 | 0.34 | 0.51 | 1.02 |
| 1 | Wt. % Zinc (Zn) | 0.22 | 0.42 | 0.82 | 1.24 | 2.47 |
| 1 | Wt. % Ammonia ($NH_3$) | 1.82 | 1.82 | 1.82 | 2.51 | 4.99 |
| 2 | Wt. % Silicate ($SiO_2$) | 0.17 | 0.34 | 0.66 | 0.99 | 1.98 |

Example 2

An ammonia-stabilized zinc and borate-containing solution each having a zinc to boron (Zn:B) mole ratio of 1:1, was prepared according to the methods of the invention, as an example of the first aqueous composition. The method of preparation was as follows.

Ammonium hydroxide (56 mL of a 30% $NH_4OH$ solution) was stirred into 200 g of deionized water. Zinc chloride (17.64 g $ZnCl_2$) was added to the water-ammonia solution and the mixture was vigorously stirred until the zinc chloride was completely dissolved. In a separate container, 6.68 g of TIM-BOR® disodium octaborate tetrahydrate (manufactured by U.S. Borax Inc.) was dissolved in 120 g of deionized water. The TIM-BOR® solution was then poured slowly with agitation into the zinc/ammonia solution, providing an essentially clear solution.

An acidified solution of sodium silicate was prepared as follows. In a separate container, a solution of 40 g of N®Silicate in 119 g of deionized water was added with mixing to a solution of 5.7 g of concentrated sulfuric acid in 119 g of deionized water. The resulting solution was the second aqueous composition.

The first aqueous composition was used to treat ¾"×¾" southern pine wood blocks according to AWPA method E11-97. The wet, treated wood blocks were then soaked in the second aqueous composition for 5-10 minutes until a gel was visible on the surface of the wood blocks. Then, the wood blocks were removed from the composition and dried overnight (about 16 hours) at 60° C. The wood blocks were then leached according to AWPA method E11-97 to produce the following results:

| Boron Loading in Wood, % BAE | Boron Retention in Wood, % BAE | % Boron Retention |
|---|---|---|
| 2.18 | 0.51 | 23.4 |

The preservative solutions of this invention are suitable for treating wood products to provide leach-resistant protection against biological attack from a variety of wood-destroying organisms, including insects and fungal decay. Various changes and modifications of the invention can be made, and to the extent that such changes and modifications incorporate the spirit of this invention, they are intended to be included within the scope of the appended claims.

What is claimed is:

1. A preservative system comprising:
   (a) a first aqueous composition comprising a source of zinc selected from the group consisting of zinc oxide and soluble zinc salts; a source of borate selected from the group consisting of zinc borate, boric acid, boric oxide and water soluble borate salts; a source of ammonia; and water; wherein the composition comprises at least 50 wt % water; and
   (b) a second aqueous composition, separate from the first composition, comprising an alkali metal silicate and water.

2. The preservative system according to claim 1, wherein the first and second compositions are essentially chloride ion free.

3. The preservative system according to claim 1, wherein the first and second compositions are essentially copper-free.

4. The preservative system according to claim 1, wherein the source of ammonia is ammonium hydroxide, the source of zinc is zinc chloride, the source of borate is sodium borate, and the alkali metal silicate is sodium silicate.

5. The preservative system according to claim 1, wherein the source of borate is disodium octaborate tetrahydrate and the alkali metal silicate is sodium silicate having an $SiO_2$:$Na_2O$ weight ratio greater than 3:1.

6. The preservative system according to claim 1, wherein the first aqueous composition comprises from about 0.1 to about 1.0 weight percent boron, from about 0.2 to about 2.5 weight percent zinc, and from about 1 to about 5 weight percent ammonia, and wherein the second aqueous composition comprises between about 1 and about 10 wt % $SiO_2$.

7. The preservative system according to claim 1, wherein zinc and boron are present in the first aqueous composition in a mole ratio Zn:B between about 0.4:1 and 5:1.

8. The preservative system according to claim 1, wherein zinc and boron are present in the first aqueous composition in a mole ratio Zn:B between about 1:1 and 3:1.

9. The preservative system according to claim 1, wherein zinc and boron are present in the first aqueous composition in a mole ratio Zn:B between about 1.5:1 and 2:1.

10. The preservative system according to claim 1, wherein silicon in the second aqueous composition and boron in the first aqueous composition are present in a mole ratio Si:B between about 0.2:1 and 0.3:1.

11. The preservative system according to claim 1, wherein ammonia and zinc are present in the first aqueous composition in a mole ratio $NH_3$:Zn between about 7:1 and 33:1.

12. A preservative system consisting of:
(a) a first aqueous composition consisting essentially of a source of zinc selected from the group consisting of zinc oxide and soluble zinc salts; a source of borate selected from the group consisting of zinc borate, boric acid, boric oxide and water soluble borate salts; a source of ammonia; and water; wherein the composition is essentially copper-free and comprises at least 50 wt % water; and
(b) a second aqueous composition, separate from the first composition, consisting essentially of an alkali metal silicate and water.

13. The preservative system of claim 12, wherein the first and second compositions are essentially copper-free.

* * * * *